United States Patent [19]

Labat et al.

[11] 4,064,159

[45] Dec. 30, 1977

[54] PROCESS FOR PREPARING ALPHA-AMINO-GAMMA-METHYLMER-CAPTOBUTYRONITRILE

[75] Inventors: Yves Labat; Aristide Boy, both of Pau, France

[73] Assignee: Produits Chimiques Du Bearn, Pau, France

[21] Appl. No.: 731,628

[22] Filed: Oct. 12, 1976

[30] Foreign Application Priority Data

Oct. 10, 1975  France .................. 75.31163
Sept. 24, 1976  France .................. 76.28786

[51] Int. Cl.$^2$ .................. C07C 121/43; C07C 120/00
[52] U.S. Cl. .................. 260/465.5 R
[58] Field of Search .................. 260/465.5 R

[56] References Cited

U.S. PATENT DOCUMENTS

| | | | |
|---|---|---|---|
| 2,542,768 | 2/1951 | Gresham et al. | 260/465.5 R X |
| 2,564,105 | 8/1951 | Gresham et al. | 260/465.5 R X |
| 2,732,400 | 1/1956 | Weiss | 260/465.5 R X |
| 3,517,048 | 6/1970 | Thoma et al. | 260/465.5 R |

Primary Examiner—Joseph P. Brust
Attorney, Agent, or Firm—Ostrolenk, Faber, Gerb & Soffen

[57] ABSTRACT

In a process for preparing alpha-amino-gamma-methylmercaptobutyronitrile by aminating, by means of ammonia, alpha-hydroxy-gamma-methylmercaptobutyronitrile at a temperature of 50° C to 100° C, the ammonia is accompanied by an amount of water corresponding to at least 1 mole per mole of ammonia.

The molar $NH_3$/cyanhydrine ratio in the reaction medium is 2 to 10, and preferably 4 to 7, the $H_2O$/cyanhydrine ratio in the reaction medium is 4 to 20, and preferably 5 to 16, while $H_2O/NH_3$ ratio is 1 to 3, and preferably 1.3 to 2. Advantageously the reaction medium is introduced into a piston-type tubular reactor which is maintained at a constant temperature, the dwelling time of the mixture in the heated zone being 1 to 30 minutes, and preferably 2 to 25 minutes, and the reaction medium is maintained under a pressure of 1 to 10 bars, and preferably a 4 to 8 bars.

9 Claims, No Drawings

PROCESS FOR PREPARING ALPHA-AMINO-GAMMA-METHYLMERCAP-TOBUTYRONITRILE

The present invention relates to an improved process for preparing alpha-amino-gamma-methylmercaptobutyronitrile, and it is more particularly related to a process for preparing the same in a continuous manner.

The alpha-amino-gamma-methylmercaptobutyronitrile, which will be designated herein after by the initials "AMN", is an important intermediary product obtained when carrying out processes for preparing methionin. This latter substance, i.e., the aminated acid having the formula:

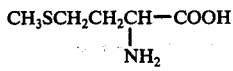

is presently more and more frequently used, especially in the field of the preparation of foodstuff for domestic animals such as bovines and fowl; consequently it is desirable to be able to prepare this compound in the most economic and rational manner possible. One of the currently used processes comprises, in one of its phases, aminating beta-methylmercaptopropional dehyde (alpha-hodroxy-gamma-mercaptobutyronitrile) cyanhydrine — which will be designated herein after by the name of "cyanhydrine" — according to the following reaction:

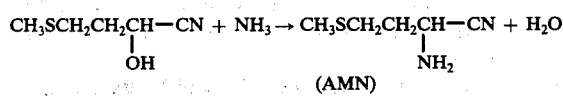

Methionine is produced by hydrolysis of the AMN obtained by the reaction set forth herein above. The starting cyanhydrine may be a result of various processes, for example of the reaction of methylmercaptan with acrolein and cyaniding of methylmercaptopropional dehyde (MMP) obtained according to a well known process, or by reacting hydrocyanic acid with acrolein followed by the action of the methylmercaptan on the resulting nitrile, or else by the simultaneous reaction of the three compounds constituted by hydrocyanic acid, acrolein and methylmercaptan.

Amination of cyanhydrine, i.e., alpha-hydroxy-gamma-methylmercaptobutyronitrile, according to the above mentioned reaction has been performed up to now by the action of anhydrous ammonia used in a large excess amount, which involved the necessity of operating under a comparatively high pressure. As indicated in U.S. Patent No. 2,485,236 which describes this known process, it has been necessary, in practice, to operate under pressures of 10 to 100 bars, generally under pressures of about 40 bars, with a view to performing the reaction within a time period of less than ½ hour. Indeed, when operating at temperatures lower than 80° C, the reaction is slow; it has been necessary to operate at temperatures of 80° to 90° C to achieving a complete reaction within 15 to 20 minutes; however in this case, the ammonia pressure is about 40 to 50 bars. Under these conditions, it has been very difficult to perform the reaction in a continuous manner. Furthermore, under these operating conditions, as far as time and temperature are concerned, the resulting product tends to colour due to formation of secondary products on account of polymerization reactions of HCN and MMP.

Other known processes for preparing AMN comprise reacting simultaneously in the same reactor MMP, hydrocyanic acid, ammonia (in the form of $CNNH_4$), or reacting MMP with ammonium cyanide, ammonium chloride and ammonia, whereas the process according to the invention consists in first preparing cyanhydrine and then aminating said cyanhydrine with ammonia.

These latter known processes do not allow operating at temperatures above 40° to 45° C, thereby entailing an increase of the dwelling time in the reactors to about 1.5 hours with a view to achieving a satisfactory conversion. When the reaction is performed at higher temperatures, with a view to decreasing this dwelling time, the reaction product will contain a high proportion of coloured substances corresponding to copolymers of the various reaction products.

The present invention provides an improvement which allows performing the amination according to the above reaction with satisfactory results, as far as the yield is concerned, while operating at substantially lower pressures and using substantially smaller amounts of ammonia, as compared to the prior processes; the process according to the invention can easily be performed in a continuous manner, while the resulting product is neither impared, or abnormally coloured. Indeed, the process according to the invention can be performed with short dwelling times, which is of paramount importance with a view to preventing the products present from undergoing undesirable changes.

The invention is based on the surprising discovery that the amination of cyanhydrine can be performed under excellent condition when the anhydrous ammonia is replaced by concentrated ammonia liquor under a comparatively low pressure. The presence of a certain amount of water in the reaction medium does not impede the reaction process, since this water is required for the hydrolysis reaction of the aminonitrile, which follows the reaction for preparing the AMN. Furthermore, this water ensures the homogeneity of the reaction medium, and thereby allows the problems of stirring, which arise in the known processes, to be solved more easily. Consequently, it is possible to use a piston-type tubular reactor. The pressure is about 1 to 10 bars, preferably 4 to 8 bars.

The improved process according to the invention thus comprises heating alpha-hydroxy-gamma-methylmercaptobutyronitrile (or MMP cyanhydrine) with an excess amount of $NH_3$ in the presence of $H_2O$ at a temperature higher than 40° C, preferably at a temperature comprised between 50° and 100° C, and particularly between 60° and 90° C.

In a preferred embodiment of the invention, the molar proportion of the $NH_3$ present is 2 to 10 moles, and more particularly 4 to 7 moles per mole of cyanhydrine used at the start, instead of at least 30 moles as in the prior processes. The amount of water may be 1 to 3 moles per mole of $NH_3$, the proportion being comprised between 1.3 and 2 moles of $H_2O$ per mole of $NH_3$. The $H_2O$/cyanhydrine ratio is comprised between 4 and 20, and preferably between 5 and 16.

When the above indicated preferred proportions are used while performing the process according to the invention at a temperature of 80° and 90° C, the pressure in the system does not exceed a value of about 3 to 5 bars. Under these conditions, the reaction can be carried out easily in a perfectly continuous manner on an industrial scale : it suffices to introduce at predetermined locations the reagents into a piston-type tubular reactor at the desired temperature, the dwelling time of the mixture in the zone wherein this temperature prevails being, e.g., 1 to 30 minutes, preferably 2 to 25 minutes; then a AMN solution can be collected at the outlet of the tube, this AMN solution being then treated in a manner known per se. The dwelling time of the reagents as indicated in following Examples is the apparent dwelling time calculated while taking into account the inlet flow rate of the liquid reagents at atmospheric pressure and ambiant temperature.

The invention will be described herein after by means of Examples which are given by way of illustration, but not of limitation.

EXAMPLES 1 to 11

Reaction mixtures are prepared by injecting beta-methylmercaptopropionaldehyde.

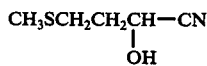

and a concentrated aqueous solution of $NH_3$ in predetermined proportions. The reagents are introduced, by means of a metering pump, into a reactor constituted by a metallic tube having an inner diameter of 4 mm, which is dipped into a bath maintained at a fixed temperature indicated in each Example. Pressure is maintained at a constant value.

The Table hereinafter indicates the molar ratios $NH_2$/cyanhydrine and $H_2O$/cyanhydrine, i.e., the respective number of moles of $NH_3$ and $H_2O$ per mole of cyanhydrine used. The cyanhydrine is prepared in a reactor, by successive batches, by reacting HCN with MMP at a temperature of about 40° to 50° C in the presence of an alkaline catalyst, as described in the prior publications.

The yield of straw-yellow aminonitrile, which is indicated in the last vertical column, is expressed in values related to the MMP initially used.

TABLE

| No. | $NH_3$ cyanhydrine | $H_2O$ cyanhydrine | Temperature (° C) | Dwelling time (mn) | Pressure (bars) | AMN yield (%) |
|---|---|---|---|---|---|---|
| 1 | 6.35 | 15.3 | 50 | 19 | 1.5 | 91 |
| 2 | 6.35 | 15.3 | 60 | 19 | 1.5 | 95.2 |
| 3 | 6.70 | 15 | 70 | 19 | 1 | 95 |
| 4 | 7 | 16.7 | 80 | 19 | 3 | 93.4 |
| 5 | 6 | 9.3 | 70 | 19 | 3 | 94.4 |
| 6 | 4 | 14 | 70 | 19 | 3 | 68 |
| 7 | 5 | 10 | 70 | 19 | 2 | 94.3 |
| 8 | 6.4 | 10 | 70 | 10 | 2.5 | 91.4 |
| 9 | 6.5 | 10 | 80 | 10 | 4 | 96 |
| 10 | 6 | 9.8 | 80 | 7 | 5 | 91.8 |
| 11 | 6.6 | 10 | 90 | 7 | 5 | 94.8 |
| 12 | 6.5 | 11 | 80 | 4 | 5 | 95.3 |
| 13 | 6.5 | 11 | 88 | 2 | 7 | 94 |
| 14 | 6.5 | 11 | 80 | 1 | 5 | 87 |

It should be noted that in Example 5 the respective reagent flow rates were, expressed in moles/hour : 2.32 for $NH_3$, 3.59 for the water and 0.386 for the cyanhydrine.

In other words, the molar ratio $NH_3$/cyanhydrine was 6, the ratio $H_2O$/cyanhydrine was 9.3 and the ratio $H_2O/NH_3$ was 1.55.

In this particular test, the volume of reaction medium which was maintained at a fixed temperature was 53.3 mol, while the total volume of the mixture in the reactor was 60.5 ml. The apparent dwelling time of the reagents in the zone maintained at said fixed temperature was 19 minutes. After 5 hours' operation, 719g reaction mixture was collected, which, when being cooled, formed two separate phases.

The results indicated in the above Table show that satisfactory results can be obtained at temperatures above 50° C, particularly already at temperatures above 60° C, provided that the $NH_3$/cyanhydrine and $H_2O$/cyanhydrine ratios present convenient values. It may thus be seen that at a temperature of 70° C, a yield of 94 to 95% can be achieved, provided that the $NH_3$/cyanhydrine ratio is comprised between 5 and 6.7 while the $H_2O$/cyanhydrine ratio is comprised between 9.3 and 15 (Examples 3, 5 and 7). On the contrary, when the $NH_3$/cyanhydrine ratio is 4 while the $H_2O$/cyanhydrine ratio is 14, which corresponds to a $H_2O/NH_3$ ratio equal to 3, the yield is substantially decreased (e.g. 68%, as in Example 6).

On the other hand, it is interesting to note that the dwelling time of the mixture in the fixed-temperature zone may be reduced to 7 minutes if the temperature is raised to 90° C and if the pressure does not exceed 5 bars (cf. Example 11). The Table also shows that the present invention allows operating at very low pressures, e.g. at pressures comprised between 1 and 1.5 bar, if desired, while even under these conditions, reaction time remains within perfectly acceptable limits, e.g. 19 minutes in the case of Examples 2 and 3. The conditions prevailing in Examples 2, 3 and 4 (high yield of 93.4, 95, 95,2%) cannot be considered as being the most favourable ones, although the pressure is only 1 bar, since the considerable amount of water involved would require large size installations.

On the contrary, Examples 9, 12, and 13 are the most interesting ones, as far the achieved AMN yield and the operating conditions are concerned. Indeed, with a $NH_3$/cyanhydrine ratio equal to 6.5, a $H_2O$/cyanhydrine ratio equal to 10 or 11 and a pressure of 4 to 7 bars, it is possible to achieve an AMN yield of about 96% by heating the reaction medium to a temperature of 80° C during 4 to 10 minutes.

It is even possible to envisage a substantially shorter dwelling time, as short as 1 minute for example (cf. Example 14). The yield is only 87%, but certains industrialists may consider that a decrease of the dwelling time can compensate a decrease in yield.

Under the most favourable operating conditions, the novel process allows a considerable reduction of the ammonia consumption to be achieved, as compared to the known processes; it allows an increased productivity to be obtained in a homogenous reaction medium.

These results allow one to clearly appreciate the importance of each one of the operating conditions, their interdependence and their influence on the yield of the reaction.

In an industrial process, the cyanhydrine itself may be prepared in a continuous manner by reacting gaseous HCN or HCN in solution with MMP, in the presence of an alkaline catalyst, in accordance with methods known per se. The reactor used may be a reactor provided with stirring means or a tubular reactor.

It will be understood that the invention is by no means limited to the content of the description herein above, and that a persn skilled in the art may make many modifications to the process as disclosed, while remaining within the scope of the invention.

What is claimed is:

1. A process for preparing alpha-amino-gamma-methylmercaptobutyronitrile by aminating, by means of ammonia, alpha-hydroxy-gamma-methylmercaptobutyronitrile at a temperature of 50° C to 100° C, wherein the ammonia is accompanied by an amount of water, the molar $NH_3$/alpha-hydroxy-gamma-methylmercaptobutyronitrile ratio in the reaction medium being 2 to 10, the $H_2O$/alpha-hydroxy-gamma-methylmercaptobutyronitrile ratio in the reaction medium being 4 to 20, and the molar $H_2O/NH_3$ ratio being 1 to 3, for 1 to 30 minutes at a pressure of 1 to 10 bars.

2. A process according to claim 1, wherein the reaction medium is introduced into a piston-type tubular reactor which is maintained at a constant temperature.

3. A process according to claim 1 wherein the molar $NH_3$/alpha-hydroxy-gamma-methylmercaptobutyronitrile ratio is 4 to 7, the $H_2O$/alpha-hydroxy-gamma-methylmercaptobutyronitrile ratio is 5 to 16, the molar $H_2O/NH_3$ ratio is 1.3 to 2 and the pressure is 4 to 8 bars.

4. A process according to claim 3 wherein the reaction medium is introduced into a piston type tubular reactor which is maintained at a constant temperature, the dwelling time of the mixture in the heated zone being 2 to 25 minutes.

5. A process according to claim 1, wherein the molar $NH_3$/alpha-hydroxy-gamma-methylmercaptobutyronitrile ratio in the reaction medium is 4 to 7.

6. A process according to claim 1, wherein the $H_2O$/alpha-hydroxy-gamma-methylmercaptobutyronitrile ratio in the reaction medium is 5 to 16.

7. A process according to claim 1, wherein the molar $H_2O/NH_3$ ratio is 1.3 to 2.

8. A process according to claim 1, wherein the reaction medium is introduced into a piston-type tubular reactor which is maintained at a constant temperature, the dwelling time of the mixture in the heated zone being 2 to 25 minutes.

9. A process according to claim 1, wherein the reaction medium is maintained under a pressure of 4 to 8 bars.

* * * * *